(12) United States Patent  
Clements et al.

(10) Patent No.: US 7,990,531 B2  
(45) Date of Patent: Aug. 2, 2011

(54) MULTI-IMAGING AUTOMATED INSPECTION METHODS AND SYSTEMS FOR WET OPHTHALMIC LENSES

(75) Inventors: Julie Ann Clements, Southampton (GB); Steven John Collier, Frodsham (GB); Jennifer Susan Marsh, St Helens (GB)

(73) Assignee: CooperVision International Holding Company, LP, St. Michael (BB)

( * ) Notice: Subject to any disclaimer, the term of this patent is extended or adjusted under 35 U.S.C. 154(b) by 256 days.

(21) Appl. No.: 12/133,596

(22) Filed: Jun. 5, 2008

(65) Prior Publication Data

US 2009/0303465 A1    Dec. 10, 2009

(51) Int. Cl.  
*G01B 11/00* (2006.01)

(52) U.S. Cl. .................. 356/239.2; 356/390; 356/124; 382/141

(58) Field of Classification Search .............. 356/390, 356/239.2  
See application file for complete search history.

(56) References Cited

U.S. PATENT DOCUMENTS

| | | | |
|---|---|---|---|
| 5,467,868 A * | 11/1995 | Abrams et al. | |
| 5,528,357 A * | 6/1996 | Davis | |
| 5,578,331 A | 11/1996 | Martin et al. | |
| 5,717,781 A * | 2/1998 | Ebel et al. | |
| 5,748,300 A * | 5/1998 | Wilder et al. | |
| 5,812,254 A * | 9/1998 | Ebel et al. | |
| 5,828,446 A * | 10/1998 | Davis | |
| 6,047,082 A * | 4/2000 | Rhody et al. | 382/141 |
| 6,154,274 A * | 11/2000 | Davis et al. | |
| 6,259,518 B1 * | 7/2001 | Russell et al. | |
| 6,301,005 B1 * | 10/2001 | Epstein et al. | |
| 6,314,199 B1 * | 11/2001 | Hofer et al. | |
| 6,471,396 B2 * | 10/2002 | Biel | |
| 6,765,661 B2 * | 7/2004 | Biel et al. | |
| 7,053,997 B2 * | 5/2006 | Suzuki et al. | |
| 7,256,881 B2 * | 8/2007 | Leppard et al. | |

(Continued)

FOREIGN PATENT DOCUMENTS

WO      WO 00/46582 A1       8/2000  
WO      WO 2007/082859 A1    7/2007

OTHER PUBLICATIONS

International Search Report completed Jan. 11, 2010 and mailed Jan. 12, 2010 from corresponding International Application No. PCT/US2009/045038, filed May 22, 2009 (5 pages).

(Continued)

*Primary Examiner* — Gregory J Toatley  
*Assistant Examiner* — Rebecca C Slomski  
(74) *Attorney, Agent, or Firm* — Klein, O'Neill & Singh, LLP

(57) ABSTRACT

A method for inspecting lenses, especially wet contact lenses provided in a volume of liquid inside a container is described. A first image of the lens at a first position in the container is obtained, the lens then being moved to a second position within the container where a second image is obtained. A computer algorithm processes the first and second images to compare features that have moved with the lens to those features that have not moved with the lens whereby lenses are rejected if a feature has moved with the lens but is not a normal feature of the lens.

25 Claims, 4 Drawing Sheets

U.S. PATENT DOCUMENTS

| | | | |
|---|---|---|---|
| 7,339,171 B2 * | 3/2008 | Biel et al. | |
| 2001/0016059 A1 | 8/2001 | Krahn et al. | |
| 2002/0146161 A1 | 10/2002 | Suzuki et al. | |
| 2002/0163638 A1 | 11/2002 | Biel et al. | |
| 2007/0195311 A1 * | 8/2007 | Morgan et al. | 356/124 |
| 2008/0137076 A1 * | 6/2008 | Clements et al. | |

OTHER PUBLICATIONS

Written Opinion completed Jan. 11, 2010 and mailed Jan. 12, 2010 from corresponding International Application No. PCT/US2009/045038, filed May 22, 2009 (4 pages).

* cited by examiner

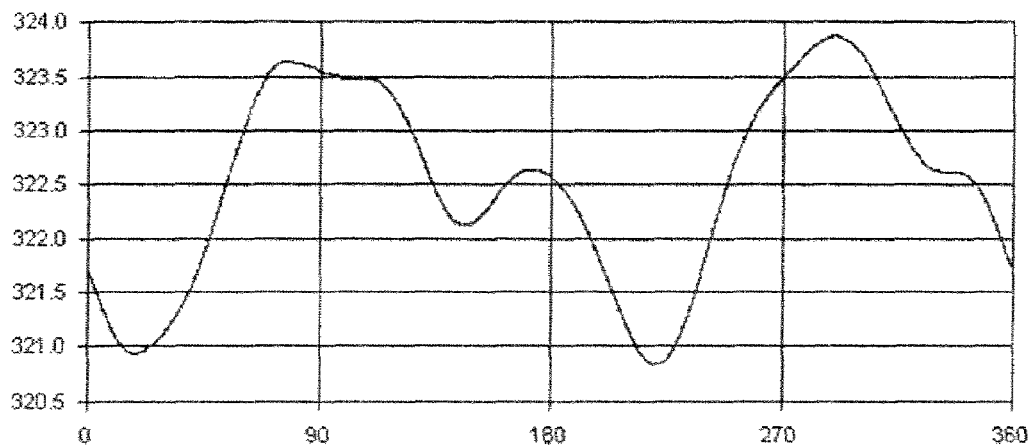
FIG. 3A
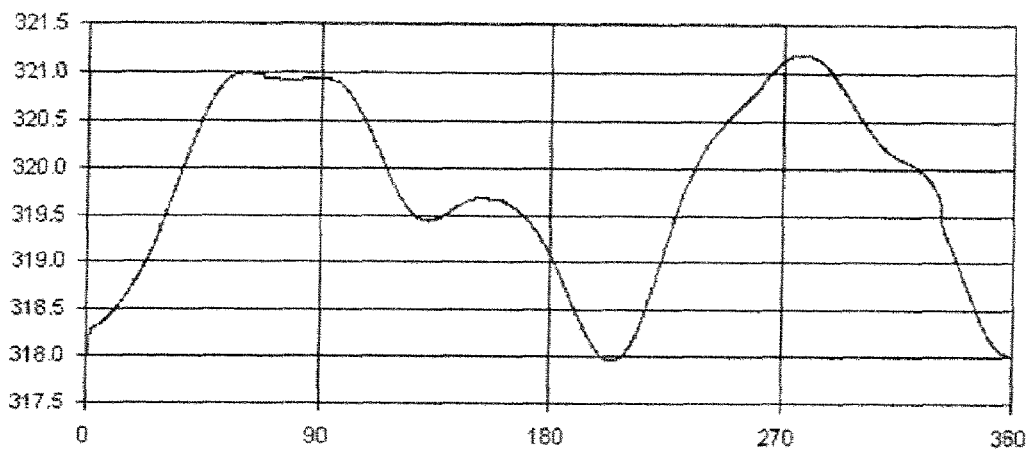
FIG. 3B
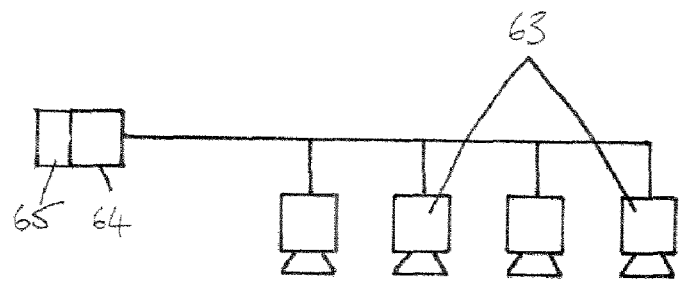
FIG. 6
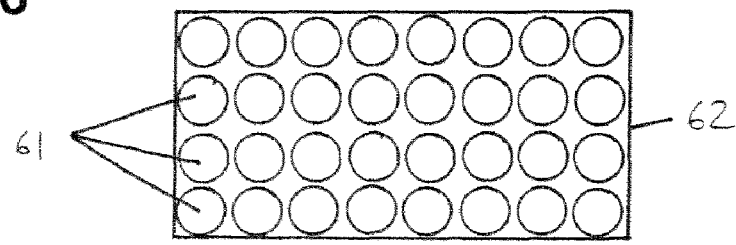

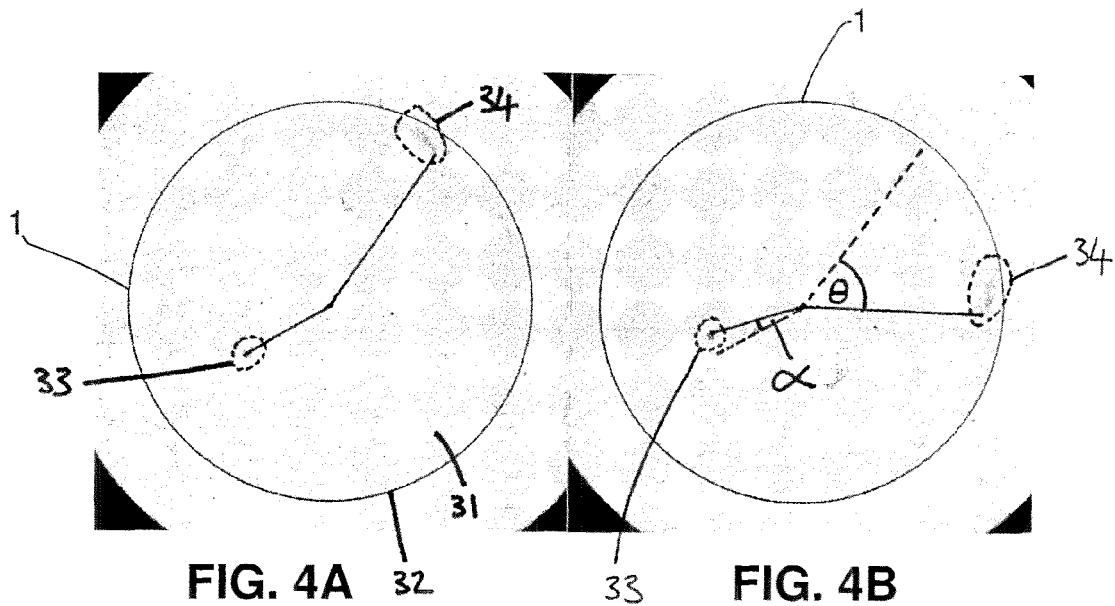
FIG. 4A  FIG. 4B
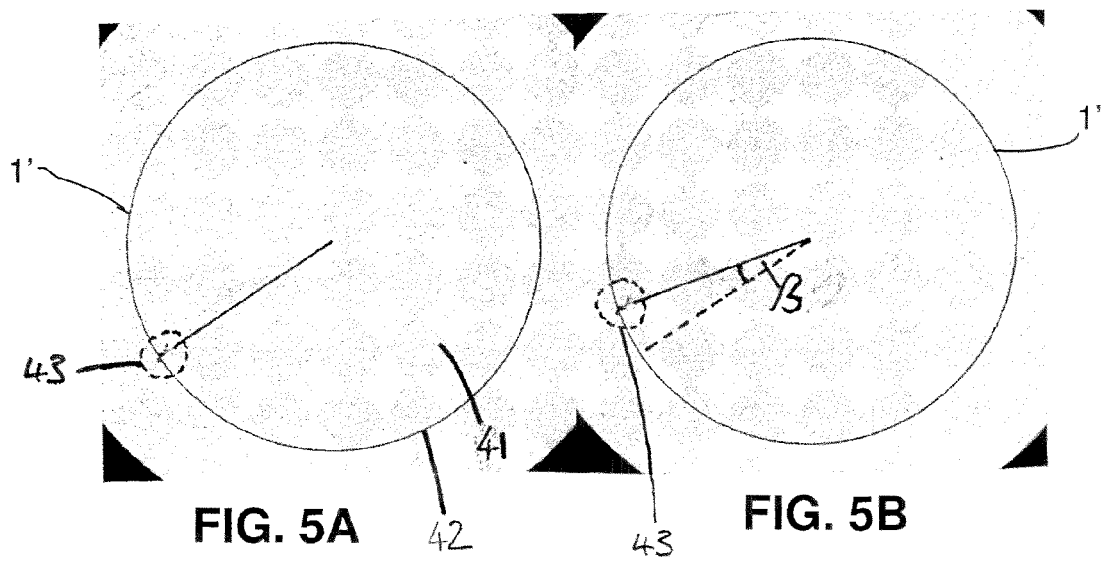
FIG. 5A  FIG. 5B

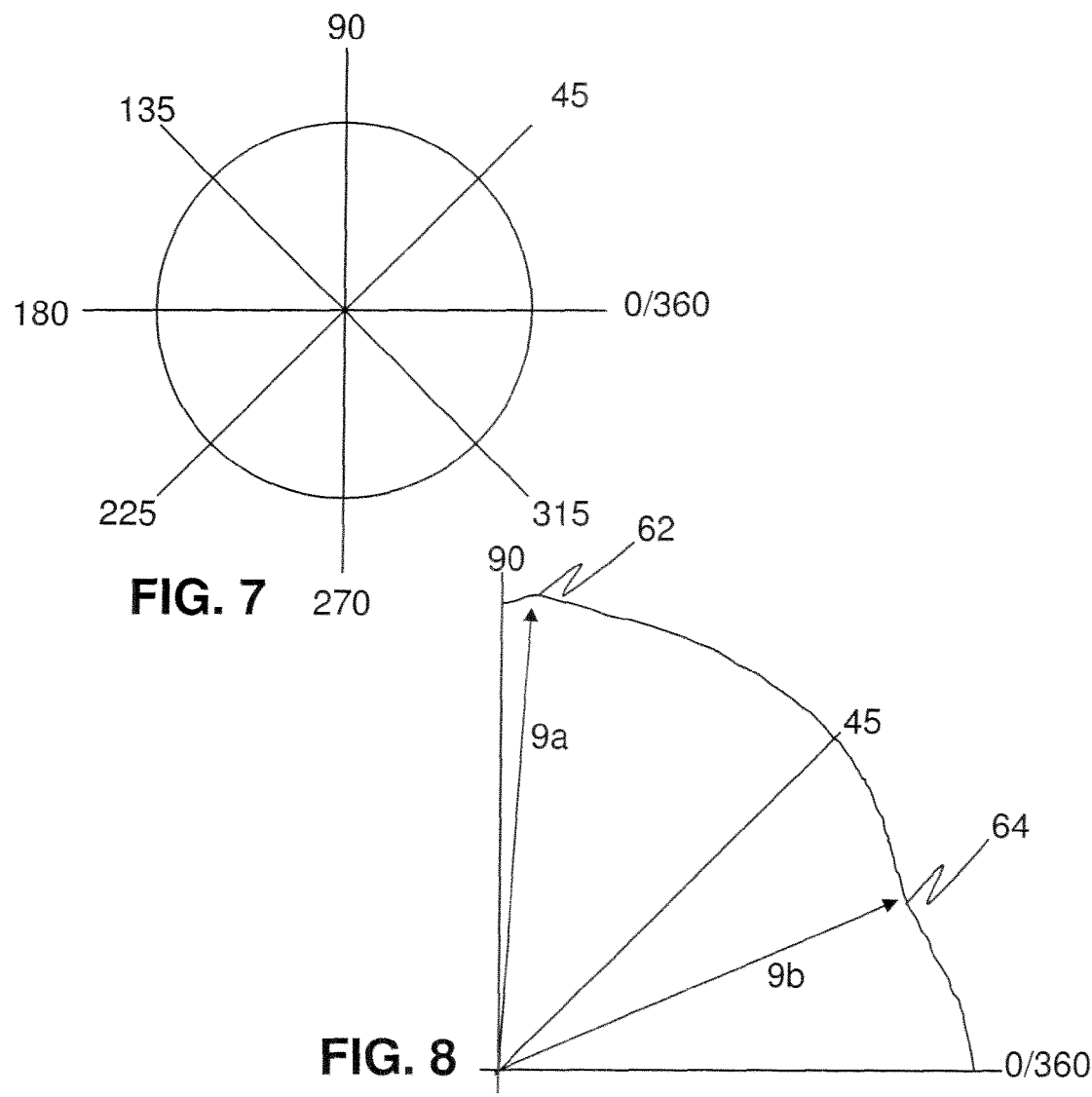
FIG. 7
FIG. 8
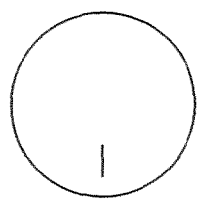 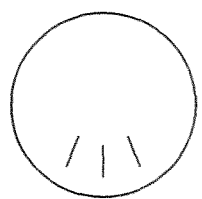 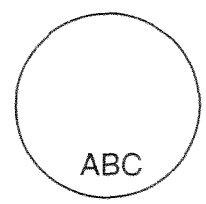 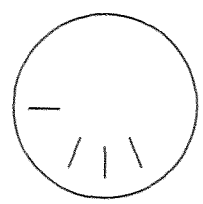
FIG. 9A  FIG. 9B  FIG. 9C  FIG. 9D

MULTI-IMAGING AUTOMATED INSPECTION METHODS AND SYSTEMS FOR WET OPHTHALMIC LENSES

FIELD

This invention relates to an automated inspection method of ophthalmic lenses, such as contact lenses, as well as automated inspection systems and software for such systems. More particularly, although not exclusively, the present methods, systems, and software relate to a multi-imaging automated inspection method for wet contact lenses or contact lenses in a volume of liquid.

BACKGROUND

In the manufacture of contact lenses, contact lenses are inspected for defects to reduce the possibility that defective lenses are distributed to contact lens wearers. A manufacturer typically determines the number of defects, or the types of defects, or both that will cause a contact lens to be rejected and discarded before distribution to a lens wearer. Unrejected lenses are passed and packaged for distribution.

Contact lens inspection can be performed manually by having a person inspect a magnified image of the contact lens prior to packaging. Contact lens inspection can be performed in an automated manner using one or more computerized devices and systems and software. Some contact lens inspection systems inspect contact lenses in a dry state, that is when the lens is not located in a volume of liquid, and some contact lens inspection systems inspect contact lenses in a wet state, that is when the contact lens is located in a volume of liquid. Automated systems and methods often involve one or more cameras that take an image or images of illuminated contact lenses that have been illuminated by one or more light sources. The images are processed by one or more computers to determine if the tenses have defects.

SUMMARY

It has now been discovered that even though contact lenses, particularly cast-molded contact lenses obtained from a lens-shaped cavity formed between a male mold member and a female mold member, are produced to a high degree of precision, each wet or hydrated contact lens in a batch of more than one wet contact lens has a unique edge profile around the perimeter of the contact lens. That is, when a wet contact lens is imaged with a camera, instead of the contact lens image having a perfectly circular perimeter where the linear radial length for each meridian of a contact lens image is the same, images of wet contact lenses, particularly cast-molded contact lenses, have linear radial lengths that randomly vary around the contact lens image perimeter. Thus, each contact lens has a unique edge shape or edge profile that can be used in the determination of whether a potential defect in a contact lens image is an actual lens defect or is an artifact present in a liquid or on the carrier cavity in which the contact lens is located. The unique profile of the lens edge is apparent on a microscopic level. For example, a contact lens may appear, when viewed without microscopic magnification to have a circular perimeter, but when viewed with magnification to reveal microscopic features, a non-circular rotational lens edge profile may be observed around the perimeter of the lens.

The present methods, systems, and software are based on this discovery in that they use the edge profiles of images of a wet ophthalmic lens to determine the amount of movement of the lens in a cavity of a container during an inspection process. By comparing the movement of the ophthalmic lens in the container to the movement of other features identified in the lens images, it is possible to reliably discriminate between actual defects of the ophthalmic lens and artifacts that may be present in the liquid or on the container cavity in which the ophthalmic lens is located.

In a first aspect, a method of inspecting an ophthalmic lens for defects comprises the steps of providing the lens in a volume of liquid within a cavity of a container, obtaining a first image of the lens at a first position in the container, causing the lens to move from the first position in the container to a second position, and obtaining a second image of the lens at the second position. In certain embodiments, the ophthalmic lens is a contact lens. Each of the first and second images comprises the entire lens edge of the contact lens. In other words, the first image comprises an image of the contact lens including the entire perimeter of the contact lens, and the second image comprises an image of the contact lens including the entire perimeter of the contact lens. When digital cameras are used to obtain the first and second images or to take pictures of the lens, the images are represented by numerical or digital values that are image data. The first and second images, or the image data, are processed with a computer algorithm, such as computer software, to locate features in the images. In other words, the method can comprise using a computer algorithm to process the first and second images to locate features in the images. The method also comprises generating lens edge profiles of the contact lens images. The lens edge profiles may also be understood to be lens edge maps. More specifically, the methods comprise generating a first lens edge profile from the first lens image, and generating a second lens edge profile from the second lens image. By comparing the first lens edge profile and the second lens edge profile, the amount of movement of the lens from the first position to the second position can be determined. The method also comprises comparing the location of corresponding features located in the first and second images to distinguish features that have moved with the lens from features that have not moved with the lens based on the amount of movement of the lens determined by comparing the first and second lens edge profiles. The features, if any, that move with the lens and are not normal lens features, are classified as a lens defect or lens defects. The lens is rejected if a predetermined number of lens defects are detected. In addition, the present methods may include obtaining more than two images of ophthalmic lenses, for example, the methods and systems may obtain three, four, five, or more images of ophthalmic lenses, which additional images can also be used during the inspection process. Using additional images may be helpful in improving the inspection accuracy, and reduce the number of false rejects.

The lens edge profiles can be represented in numerical or graphical form. As used herein, a lens edge profile refers to the shape of the perimeter of the contact lens, that is along the peripheral lens edge of the contact lens. The perimeter of the contact lens has a certain thickness or band. As used herein, an inner edge refers to the edge internal to the band and closer to the center of the contact lens: and an outer peripheral edge refers to the edge external to the band and further from the center of the contact lens. The lens edge profile is generated by measuring a linear radial distance from the center of the image of the contact lens, such as from the optic axis of the contact lens image, to the outer peripheral edge of the contact lens image, to the inner edge of the contact lens image, or both the inner edge and outer peripheral edge of the contact lens image, along a plurality of meridians, such as from a plurality of meridians from 0 degrees to 360 degrees. The number of meridians used to measure the linear radial length can vary; however, it can be understood that measuring relatively more meridian radial lengths will provide a lens edge profile that more accurately describes the shape of the contact lens perimeter. For example, measuring the linear radial length of 360 meridians in 1 degree increments will provide a more accurate lens edge profile than measuring the radial length of 4 meridians in 90 degree increments.

The features located in the first and second images may include potential defects in the lens. The features located in the first and second images may also include artifacts present in the liquid or on or in the container that were in the field of view of the camera taking the pictures of the lenses. The features may also include one or more identifying marks provided on the lens, such as a mark or marks used to identify the rotation of the lens when the lens is worn on an eye of a lens wearer, or a mark or marks that may provide other information to the lens wearer, lens manufacturer, or optometrist or ophthalmologist viewing the lens.

The method thus involves automated recording (e.g., taking a picture or pictures) and comparing two images of the lens (e.g., two individual images of one lens), the lens having been moved between recording the two images, in order to distinguish defects in the lens from artifacts present in the liquid or the container or both the liquid and the container.

Discrimination between an actual lens defect and an artifact can thus be achieved by identifying a potential defect in the first lens image, identifying the potential defect in the second lens image, and classifying the defect as an artifact if the potential detect is in the same relative position for both the first and second lens images. Potential defects may be identified based on any suitable criteria, including one or more criteria selected from the following: defect size, defect orientation, defect shape, and the like.

It may be that the first and second images are only compared when a potential defect is detected in both images; thus if no potential defects are detected, the lens may be passed, and the two images not compared if no potential defect is detected in the first image.

The movement of the lens from the first position to the second position may be movement relative to the container. In other words, in some embodiments, it is desirable to have a different spatial relationship between the lens and the container when the first and second images are acquired. The movement can be rotational (e.g., about the optic axis of the lens) or translational (e.g., at least approximately in a plane perpendicular or nearly perpendicular to the optic axis of the lens), or both. The movement of the lens may be achieved by moving the container in which the lens is located. For example, if the lens is located in a liquid in a cavity of a container, and the container is located on a tray or other suitable container carrier, the movement of the lens may be achieved by fast rotation of the tray, vibration of the tray, or any other suitable method, and combinations thereof. The movement of the lens can be caused by moving the tray at a relatively high acceleration rate, a relatively high deceleration rate, or both. The acceleration and deceleration is likely to cause relative movement of the lens, the liquid in which the lens is located, and the lens container. In a manufacturing process where it is desirable to maximize throughput of the lenses being produced, it is desirable to perform the movement or rotation in a time period of about 1 second or less. For example, the movement of the container can be on the order of milliseconds or hundreds of milliseconds, and the movement can cause the lens to move for a time period greater than 1 second.

In certain embodiments of the present methods, the lens is moved or rotated by moving a carrier or tray on which the lens container is disposed in a circular path. For example, the carrier or tray can be moved in a horizontal circular path having a diameter less than about 100 mm, such as about 80 mm, about 60 mm, about 40 mm, or about 20 mm. In other words, the carrier or tray may be oriented horizontally so that liquid can be retained in the lens container, and the carrier or tray can be moved in a circular path while maintaining the carrier or tray in the horizontal orientation (e.g., so liquid doesn't spill from the carrier or tray). In one specific example, the container carrier or tray rotates in a substantially horizontal circular path having a diameter of about 20 mm or about 25 mm. In other embodiments, circular paths are not required, for example, the carrier or tray may move in an elliptical path or other geometric shape. In some of these embodiments, including the illustrated embodiment, the container carrier or tray is not rotated. Instead, the orientation of the carrier is fixed, but the carrier as a whole is moved in a circular path about a central axis. Or, the tray or carrier may be vibrated or the tray may move in a linear direction in a horizontal or nearly horizontal plane. The movement of the carrier causes the lens within the containers to rotate within the liquid in the container.

In other embodiments, the fast rotation may be effected by causing rotation of the tray by more than 10 degrees and then returning the tray to its original position with a time of less than two seconds.

After the lens begins to move, a camera may then acquire two images of the moving lens. Alternatively, a camera may acquire a first image of the lens before it is caused to move and then acquire a second image of the lens as the lens is moving, such as rotating, or after it has moved.

The method may include the step of thresholding the first and second images in order to locate the features; that is, a threshold darkness may be set, and anything darker than said threshold may be identified as being of interest as potential defects.

The method may include the step of identifying the lens edge in the first and second images and locating deviations from an expected edge shape. Such deviations may be identified as potential defects.

The container may be at the same location when the first and second images are obtained. Alternatively, the container may be in a first location when first image is obtained and in a second, different location When the second image is obtained; the lens may then be caused to move from the first position to the second position by the movement of the container from the first location to the second location.

The contact lens may be stored or packaged in a liquid. The lens may be a polymerized hydrogel contact lens or a polymerized silicone hydrogel contact lens.

Any movement of the lens is helpful in the present methods. In certain embodiments, the movement of the lens is only translational. In other embodiments, the movement of the lens is only rotational, such as rotation about the central optical axis of the lens. In additional embodiments, the movement of the lens is rotational and translational. Typically, in reference to the present methods and systems, rotational movement of the lens is preferred compared to translational movement of the lens. However, translational movement of the lens within the container is also useful in practicing the present methods since the images of the lenses in the containers do not require precise positioning of the lens in the container. For example, the cameras can include a field of view that includes the contact lens, the cavity in which the lens is located, and the surrounding portions of the container.

In the present methods, the contact lens may be a spherical contact lens, or a contact lens that includes an aspherical surface portion. In some embodiments, the contact lens has a toric optic zone effective in correcting astigmatism, such contact lenses are conventionally referred to as toric contact lenses. Whereas spherical contact lenses may not include identifying marks, as described herein, toric contact lenses are typically provided with one or more identifying marks, such as one or more identifying marks to visualize rotation of the contact lens when the contact lens is located on an eye. In the present methods, when the contact lens comprises an identification mark, the mark may then be one of the features located in the first and second images. The movement of other of the located features may then be determined relative to the mark, if desired. It can be understood that identifying marks are considered normal features of the contact lens since the marks are intentionally provided on the contact lens during the manufacture thereof. Features that are not normal features of the contact lens are features that are not intentionally provided on the contact lens during the manufacture thereof, among other things. In view of the above, if an identification mark is provided on the ophthalmic lens, the present methods can include a step of identifying the mark as a feature other than a defect. In addition, the present methods can include a step of measuring the movement of features relative to an identifying mark provided on the ophthalmic lens in addition to measuring radial dimensions of the lens image to generate the lens edge profiles.

Analysis of the first and second images or the image data is performed using computer software. The image analysis of both images may occur after the second image is obtained, or the images may be analyzed sequentially (e.g., such that the first image is analyzed before or during obtaining the second image and the second image is analyzed after the second image is obtained).

The location of the features in the first and second images may be made in terms of any suitable co-ordinate system, for example Cartesian coordinates or polar coordinates.

The container may be a blister pack. The container may be a lens carrier or tray having a cavity or receptacle for storing an ophthalmic lens in an aqueous solution. In certain embodiments, the container is a blister pack that comprises a contact lens storage cavity. In other embodiments, the container may be a cuvette. A packaging liquid, such as a saline solution or a buffered saline solution (e.g., phosphate buffered saline solutions, borate buffered saline solutions, and bicarbonate buffered saline solutions), any of which may include or be free of a surfactant, is provided in the cavity, and a contact lens is disposed in the packaging liquid.

The first and second images may be obtained using a camera or cameras. Typically, the images are obtained of a lens in an unsealed container. The camera can be a digital camera, and may include a charge-coupled device (CCD) array for recording the images, or the camera or cameras may include one or more complementary metal oxide semiconductor (CMOS) integrated circuits. In the illustrated embodiment, the cameras are digital cameras that include a CCD array for recording the images. The camera may be arranged to have a depth of field sufficiently large to acquire an image in which both the lens edge and the lens surface are in focus simultaneously. For example, a single image of the lens will include details of both the entire lens surface and the entire lens edge, in comparison to other dual imaging techniques which obtain separate images of the lens edge and lens surface.

The first and second images may each be of an area sufficiently larger than the lens so that accurate positioning of the lens under the camera is not critical.

A light source, for example a light-emitting diode (LED), may be used to generate a bright field image of the wet lens. The light may be at least partially collimated by a collimating lens (for example an achromatic doublet lens) and then pass through the container. For example, it can be understood that the light that the container receives is partially collimated light that has passed through the collimating lens. The container shape (e.g. a blister pack cavity shape) and the liquid in the container may together complete collimation of the partially collimated light as the light is directed from the light source to the camera. Including a contact lens in the liquid in the cavity disrupts the collimated light (the light passing through the container and liquid) and causes features of the lens to be made visible, such as the lens edge and potential defects. By disrupting or causing deviation of the light away from the camera, the lens features of the lens can be captured by the camera or cameras and processed further. The camera or cameras receive collimated light (light passing through the collimating lens, the container, and the liquid), and deviations of the collimated light due to the presence of potential defects, the lens edge, or both, enable the camera or cameras to capture those features for image processing and analysis.

In accordance with the disclosure herein, the present methods may be understood to include a step of mapping the lens edge by calculating the radial distance around the circumference or perimeter of the lens of the lens image. This can also be referred to as generating a lens edge profile. The radial distance refers to the distance from the center of the contact lens to the edge of the ophthalmic lens along a meridian of the lens. As understood by persons of ordinary skill in the art, a meridian of the ophthalmic lens can be identified by its angular measurement where 0 degrees and 360 degrees are at the 3 o'clock position and the 90 degree meridian is located at the 12 o'clock position. The radial distance can be the linear radial distance, such as when a two dimensional image of the lens is used to measure the radial distance, or the radial distance can be a curved radial distance if the curvature of the lens is included in the measurement. Those values can be used to determine the lens edge shape based on conventional edge detection techniques, such as techniques using a Sobel filter or differentiation, as understood by persons of ordinary skill in the art. These detection techniques are written into software for computers.

In practice, the lens edge can be identified by the location of, for example, its outer edge, its inner edge, its thickness (the distance between the outer edge and the inner edge) or by its darkness. However, edge thickness and edge darkness can appear to change between the first and the second image. It has now been found that desirable results can be obtained by determining the change in orientation of the lens by identifying features forming part of the outer edge of the lens. In addition or alternatively, desirable results can be obtained by comparing the inner and outer edge data to validate the angle of rotation of the lens or lens image, among other things.

The container may be carried on a tray or carrier. Very small movements of the tray carrying the container under an inspection camera may cause the lens to rotate in the container cavity, with the camera recording the first and second images, during that rotation.

The method may include the step of classifying a feature that moves by more than a minimum angular shift relative to the ophthalmic lens as a non-lens feature. Or, the method may include a step of identifying any feature which moves by more than a minimum angular shift, relative to the angular rotation of the lens, and categorizing, classifying, or labeling a feature that moves more than the minimum angular shift as a "non-lens defect" (e.g., the feature is not a lens defect, and instead is something else, such as a particle in the packaging liquid and the like). The minimum angular shift may for example be ±0.1°, ±0.5°, ±1° or ±5°, or any value between 0.1° and about 5° (e.g., in either direction). The actual value can vary based on the signal to noise ratio. Thus, for example, taking 1° as the minimum angular shift, if the lens moves by 30° between the first and second images, and the feature moves by between 29° and 31°, the angular shift of the feature is less than 1° and the feature may be considered to be or categorized as a lens defect. In comparison, if the feature moves by less than 29° or more than 31°, than the feature is categorized as a non-lens defect. If the minimum angular shift is greater than ±5°, the number of false rejects may increase, and if desired, steps of the inspection method can be repeated, such as obtaining the images and generating lens edge profiles to reduce the possibility of false rejects.

The first and second images may have a resolution on the order of micrometers or microns. In the present methods and systems, each pixel of the lens images corresponds to a distance of about 22 microns. Fine details observable at that high resolution may be used for edge mapping. When additional images are obtained using the present methods and system components, the additional images may also have a resolution on the order of micrometers.

In the illustrated embodiments, analysis of the lens edge shape and the control of the inspection systems and system components are performed using computer software.

In view of the disclosure herein, it can be understood that an embodiment of a method of inspecting an ophthalmic lens for defects comprises obtaining at least two images of one wet or hydrated ophthalmic lens in an aqueous liquid of an ophthalmic lens container, and causing the one hydrated ophthalmic lens to move within and relative to the container so that one of the images represents the lens at a first position within the container, and a second of the images represents the lens at a different second position within the container. Each of these two images includes the entire lens, for example a surface of the Lens and an edge of the lens. The method comprises analyzing the images or image data (for digital images) for potential lens defects. If a potential lens defect is categorized as a lens defect, the lens is rejected. Otherwise, the lens is deemed acceptable and is further processed in a manufacturing line. The method comprises a step of mapping the lens edge or generating a lens edge profile, such as by processing the lens image data using one or more computers, to determine the relative movement of the lens within the container, the relative movement of any potential lens defect, or both. The method can be repeated for multiple ophthalmic lenses, such that multiple lenses can be inspected at the same time or substantially the same time. This may be particularly beneficial in the manufacture of large numbers of ophthalmic lenses.

It can also be understood that another embodiment of the present methods comprises a step of mapping an edge of an image of a wet or hydrated ophthalmic lens to determine the amount of rotation of a lens in a lens container. As described herein, such methods may comprise a step of moving the hydrated ophthalmic lens from a first position in the container to a second position in the container and obtaining a first image of the lens at the first position, and a second image of the lens at the second position. The mapping step can be performed on both images or just one of the images, in certain situations. The mapping can be performed after both images are obtained by a camera, or the mapping can be performed on each image after each has been obtained, such as after the first image is obtained, and subsequently after the second image is obtained.

However, as discussed herein with respect to the illustrated embodiments, the image data of the first image of the ophthalmic lens is analyzed before the second lens image is obtained. If the analysis does not identify any potential lens defects, the lens is approved and can proceed in the manufacturing process. If the analysis identifies a potential lens defect, the lens edge of the first image can be mapped using computer software to analyze the lens image data, and the lens edge can be mapped again after moving the lens in the container and obtaining a second image of the lens using the same process for mapping the lens edge of the first image. The two lens edge maps can be correlated to each other in addition to any potential lens edge defects identified. If the potential lens defect is determined to be a lens defect, the lens is rejected. If the potential lens defect is determined to be an artifact resulting from the liquid or the container, the lens is accepted and is further processed in the manufacturing line.

In another aspect, an automated lens inspection system for performing the present methods is provided. The lens inspection system may comprise a camera, a light source, and a carrier capable of moving a lens in a lens container from a first position in the container to a second position in the container. The camera may be arranged to receive light from the light source via the lens carrier, for example by being arranged on the opposite side of the lens carrier compared to the light source.

The lens inspection system may also include a processing unit for receiving and processing images taken by the camera. The processing unit may have a first processing module for detecting features in the images taken by the camera. The processing unit may have a second processing module for ascertaining movement of the lens by comparing a first lens edge profile generated from the first lens image and a second lens edge profile generated from the second lens image. The processing unit may have a third processing module for comparing the movement of the features detected by the first processing module to the movement of the lens as ascertained by the second processing module. The processing unit may be in the form of, or define part of a computer. The processing unit may be in the form of a programmable processing unit running software in order to provide the function of the three processing modules. As an example, one or more cameras can be connected to one or more computers that include instructions, such as software, that helps control the image acquisition of the hydrated lenses, and analyzes the lens image data for potential defects.

In another aspect, a software product is provided. The software product may comprise a first software module for causing the computer to detect features in images of lenses stored on the computer. The software product may comprise a second software module for causing the computer to ascertain movement of a lens by comparing a first lens edge profile generated from the first lens image and a second lens edge profile generated from the second lens image. The software product may comprise a third software module for causing the computer to compare the movement of the features detected as a result of execution of the first software module to the movement of the lens as ascertained by the execution of the second software module.

It will be appreciated that aspects of the present methods are equally applicable to the present systems and software and vice versa.

BRIEF DESCRIPTION OF THE DRAWINGS

Certain illustrative embodiments of the present methods, systems, and products will now be described in detail, by way of example only, with reference to the accompanying schematic drawings, in which:

FIGS. 3A and 3B are graphs showing an outer edge plot of a typical lens wherein the X-axis represents the degrees about the optic axis of the lens, and the Y-axis represents a unit radial length (pixels) of the lens image;

FIGS. 4A and 4B show images of a contact lens located in a liquid of a container cavity, the images captured by the system illustrated in FIG. 2 where a lens defect is found;

FIGS. 5A and 5B show images of a contact lens located in a liquid of a container cavity, the images captured by the system illustrated in FIG. 2 where a non-lens defect is found (e.g., the detected feature is not a defect of the lens);

FIG. 6 illustrates an automated lens inspection system for inspecting many lenses in parallel;

FIG. 7 is an illustration of a plan view image of an ophthalmic lens with different meridians being identified between 0 degrees and 360 degrees, where the meridians intersect at the center of the contact lens;

FIG. 8 is a magnified view of an ophthalmic lens edge extending from the 0 degree meridian to the 90 degree meridian, and providing an illustration of a lens edge profile similar to the profile depicted in FIG. 3A between the 0 degree meridian and 90 degree meridian; and FIGS. 9A, 9B, 9C, and 9D are each illustrations of a plan view of a contact lens showing one or more identification marks on a surface of the contact lens.

DETAILED DESCRIPTION

The following description will be provided in the context of cast molded hydrogel contact lenses or cast molded silicone hydrogel contact lenses. In a cast molding process, after polymerization of a polymerizable lens precursor composition in a contact lens mold assembly, having first and second mold sections coupled together to form a contact lens shaped cavity with the composition disposed therein, the mold sections are demolded so that the polymerized contact lens product remains attached to only one of the mold sections. The polymerized contact lens product is then delensed or separated from one of the mold sections to which it is attached. The delensed polymerized contact lens product may then be inspected in a dry inspection process (e.g., when the lens is not in a hydrated state) if desired. The delensed lens product (and possibly inspected dry lens product) is then placed in a liquid, which can be in a contact lens packaging container, or can be in a extraction/hydration station of a contact lens manufacturing line. The liquid can be an aqueous liquid, such as a contact lens packaging liquid, or the liquid can be an organic solvent, such as alcohol and the like, especially for silicone hydrogel contact lenses. If the delensed lens product is placed in a liquid of an extraction hydration station, such as in a extraction tray and the like, the final hydrated contact lens can subsequently be placed in a contact lens packaging container. After the contact lens is placed in a container, it can be inspected using the methods described herein.

Figure 1:
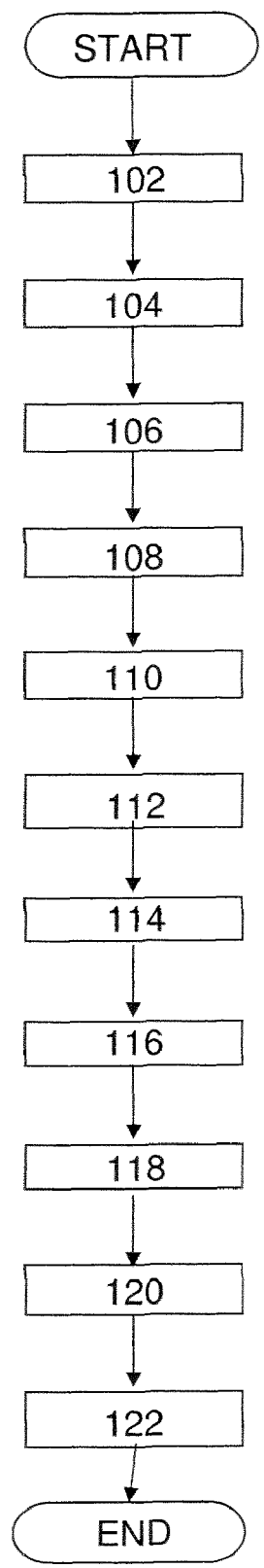
FIG. 1 is a flow chart of an embodiment of the present methods.

FIG. 1 provides a flow chart illustrating steps of an embodiment of the present methods of inspecting hydrated ophthalmic lenses for lens defects during the production thereof. As shown in FIG. 1, a method of inspecting a lens for defects comprises a step 102 of providing a lens in a volume of liquid in a cavity of a container. The lens can be placed in a receptacle or cavity of the container before adding the liquid, or the lens can be placed in the volume of liquid contained in the container. Alternatively, the lens and the liquid can be placed in the container cavity at the same time. The liquid, as discussed herein, can be any aqueous solution. For example, the liquid may be an aqueous solution that is free of preservatives or disinfectants, for example, the liquid may not be a lens cleaning solution. In certain embodiments, the liquid used in the present methods is a contact lens packaging solution, such as a saline solution or buffered saline solution, which may include or be free of one or more surfactants.

With the lens provided in the liquid in the container, the method comprises a step 104 of obtaining or recording a first image of the lens at a first position, such as by taking a picture of the lens at the first position with a camera. The method also comprises a step 106 of causing the lens to move, or moving the lens, from the first position in the container to a second position in the container, and a step 108 of obtaining or recording a second image of the lens at the second position, such as by taking a picture of the lens at the second position with a camera. As discussed herein, additional methods may include obtaining more than two images of the lens. The lens can be caused to move prior to obtaining the first and second images. For example, the lens can be caused to move, and a camera can take a first picture to obtain an image of the lens at a first time, and subsequently take a second picture to obtain the second image of the lens at a second time. Or, the lens can be provided in a fixed position prior to taking the first picture, the camera can take the first picture to obtain the first image, and the lens can be caused to move, and then the camera can take the second picture to obtain the second image. When digital cameras are used to take the pictures of the lenses, as described herein, the digital images will be recorded as numerical values using one or more computerized devices, as understood by persons of ordinary skill in the art.

The method of inspecting a lens also comprises a step 110 of processing the first and second images with a computer algorithm or computer software to locate features, such as potential lens defects and the like, in the obtained images. For example, the method may comprise using a computer algorithm to process the first and second images or image data. As described herein, the computer algorithm or software can process the numerical values corresponding to digital images of the photographed lens to locate features, such as potential defects, in the lens images or present on the lens, the container, or the container liquid.

The method also comprises a step 112 of generating a first lens edge profile from the first image, and a step 114 of generating a second lens edge profile from the second image. By comparing the first lens edge profile and the second lens edge profile, the method comprises a step 116 of determining the amount of movement of the lens from the first position to the second position. When more than two images are obtained, methods may include additional steps of generating additional numbers of lens edge profiles.

The method also comprises a step 118 of comparing the location of corresponding features located in the first and second images. The comparing 118 facilitates distinguishing features that moved with the lens from features that have not moved with the lens based on the amount of movement of the lens determined by comparing the first and second lens edge profiles.

When features have moved with the lens, and which are not normal features of the lens, the method comprises a step 120 of classifying the feature or features as a lens defect. The method comprises a step 122 of rejecting the lens if the lens includes a pre-determined number of lens defects. The pre-determined number of defects can be one or more depending on the type of defect, the size of defects, and the like, as determined by the manufacturer based on manufacturing protocols and standards.

Figure 2:
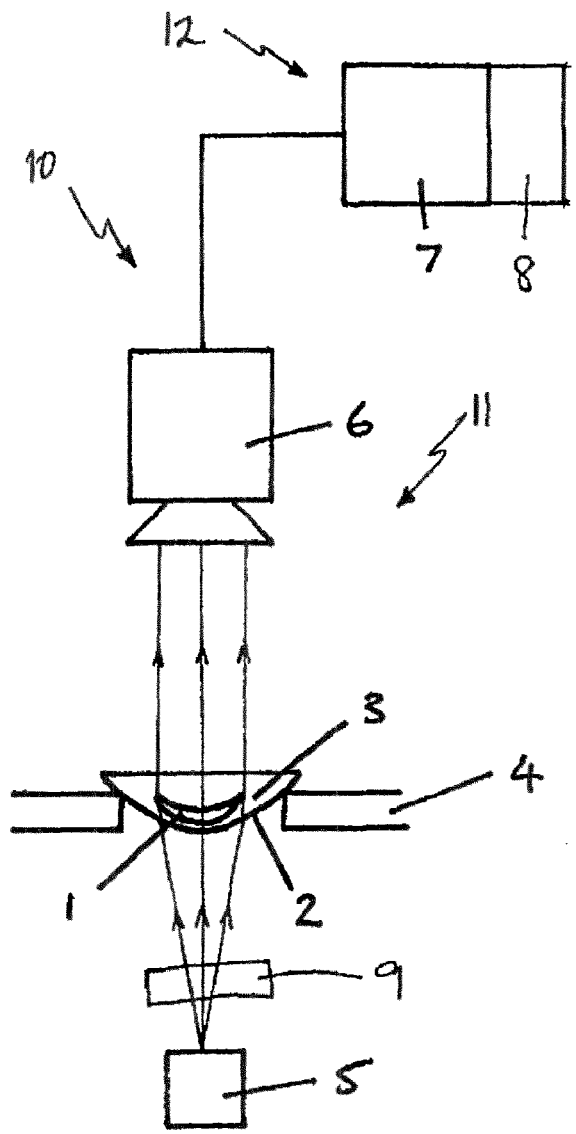
FIG. 2 is an embodiment of a lens inspection system.

FIG. 2 shows an embodiment of an automated lens inspection system. In this embodiment, the system 10 is shown with a contact lens located in a liquid provided in a container cavity, wherein the image of the contact lens is being obtained by a camera, such as a digital camera. In other embodiments of the present systems, the systems do not include the contact lens or container, and the system can be understood to include the other components described herein. Contact lenses in containers can be passed through such lens inspection systems as part of the manufacturing process of the contact lenses.

An automated lens inspection system 10, in accordance with the present disclosure, can be understood to include a lens image acquisition component 11 and a lens image analysis component 12.

The image acquisition component 11 can be understood to include a tray or carrier 4 for holding one or more contact lens containers 2, such as contact lens blister packs, prior to closing the containers, such as prior to sealing the blister packs. Alternatively, if desired, the carrier 4 can hold one or more contact lens inspection trays having cavities to store the contact lenses in liquids. The image acquisition component also includes one or more light sources 5, such as one or more LEDs located on one side of the contact lens container 2, and one or more cameras 6 located on the opposite side of the contact lens container 2. Typically, the number of light sources is equal to the number of cameras such that there is a one to one relationship. The cameras are positioned relative to the light source such that when a contact lens container is located therebetween, light emitted from the light source passes through the contact lens container toward the camera. The camera can then acquire an image of the contact lens. In certain embodiments, including the illustrated embodiments, a light collimation lens 9 is located between the light source and the contact lens container, as discussed herein. The cameras are digital cameras, which are coupled to one or more computers of the image analysis component 12. The digital cameras can be coupled by a wired connection, such as by a gigabit Ethernet connection, a USB connection, or another type of Ethernet connection; or a wireless connection, as understood by persons of ordinary skill in the art.

A camera acquires or records an image of a contact lens. The image is represented by numerical values and is stored in the computer memory. The numerical values can also be used to generate a digital image of the contact lens on a computer display or monitor. The numerical values provided by the camera correspond to pixel intensity. The camera using one or more computer protocols can communicate the numerical values or data to the image analysis component 12 for further processing, as described herein. The computer or computers of the image analysis component 12, which are directly or indirectly coupled to the camera can, through software, control the image capture by the camera, control the transmission of the image data from the camera to the computer, perform the analysis of the lens image data, and classify the lens images or features of the lens images using one or more algorithms. The software may also provide communication with other computers or components of the inspection system, such as to provide automated control of the illumination of the lens being inspected or automated control of an indexing system that can position the lenses between the camera and light source.

In more detail with reference to FIG. 2, an automated contact lens inspection system includes a contact lens 1, in this case the lens being a hydrated silicone hydrogel contact lens. Examples of silicone hydrogel contact lenses include lenses made from materials having the following United States Adopted Names (USANs): balafilcon A (PUREVISION, Bausch & Lomb), lotrafilcon A (NIGHT & DAY, CIBA Vision), lotrafilcon B (O2OPTIX, CIBA Vision), galyfilcon A (ACUVUE ADVANCE, Vistakon), senofilcon A (ACUVUE OASYS, Vistakon), narfilcon A (Vistakon), comfilcon A (BIOFTNITY, CooperVision), and enfilcon A (CooperVision). In other embodiments, the contact lens is a hydrogel contact lens that is free of a silicone component. Examples of hydrogel contact lenses include contact lenses made from materials having a US Adopted Name (USAN) such as polymacon, tetrafilcon, ocufilcon, vifilcon, etafilcon, omafilcon, alphaphilcon, nelfilcon, hilafilcon, tefilcon, or vasurfilcon, for example. Frequently, conventional hydrogel contact lenses are the polymerized product of a lens precursor composition containing hydrophilic monomers, such as 2-hydroxyethyl methacrylate (HEMA), methacrylic acid (MA), N-vinyl pyrrolidone (NVP), polyvinyl alcohol (PVA), polyvinyl pyrrolidone (PVP), and combinations thereof. The precursor compositions also frequently contain one or more catalysts, initiators, and crosslinking agents.

The lens 1 is in a first position in a container 2, the container 2 being a standard transparent or translucent contact lens blister pack, such as a polypropylene blister pack. The container 2 also holds a liquid A the liquid 3, being a contact lens packaging solution, such as a 0.9% to 1.0% buffered saline solution. The container 2 is held on or in a tray or carrier 4. There is an LED light source 5 located to one side of the lens 1 (that is closer to the convex lens surface as illustrated in FIG. 2) and a CCD camera 6 (i.e., a camera having a charge-coupled device (CCD) array for capturing lens images) located on the other side of the lens 1, the CCD camera 6 being connected to a processing unit 7 which includes a memory unit 8. A collimation lens 9 is located between the light source 5 and the container 2. The processing unit 7 and memory unit 8 can be understood to be components of the image analysis component 12.

A method of inspection proceeds as follows. The LED light source 5 transmits non-collimated visible light towards the contact lens container. The collimation lens 9 causes the light passing therethrough to be partially collimated. The partially collimated light is then directed through the container 2, the hydrated contact lens 1 and the liquid 3. The shape of the container 2, especially the bottom surface of the container 2, and the liquid 3 are such that the light becomes fully collimated as it passes through them. The contact lens 1 disrupts the fully collimated light such that an image of the lens, including the lens edge and any potential defects, are imageable by the camera 6. The CCD camera 6 is arranged such that it is capable of receiving the light that passes through the contact lens 1 and the container 2 and liquid 3 from the LED light source 5. The depth of field of the CCD camera is such that both the lens edge and the lens surface are in focus simultaneously. The distance between the camera and the contact lens container is selected so that the camera's field of view includes the entire opening, or almost all of the entire opening, of the contact lens container so that it doesn't matter where the lens is located within the container cavity. In certain embodiments the camera's field of view is at least 50% greater than the lens diameter. In further embodiments, the camera's field of view is about 60% greater than the lens diameter. Thus, for a lens having a diameter from about 13 mm to about 15 mm, the camera's field of view will be from about 20.8 mm to about 24 mm. For a contact lens having a diameter of about 14 mm, the camera's field of view is at least 21 mm, such as about 22.4 mm. The CCD camera 6 records a first image of the contact lens 1 and the container 2 as a plurality of numerical values, as described herein. The data or numerical values are delivered to the processing unit 7 of the image analysis component 12.

Once the first image has been recorded or obtained by the CCD camera 6, the lens 1 moves to a second position. Movement of the lens from the first position to the second position can be effected by moving the tray 4 holding the container 2 in a tight circular path, by vibrating the tray, or by another movement of the tray. In certain embodiments, the tray is moved before the first image is obtained by the camera. In other embodiments, the tray is moved after the first image is obtained by the camera. The movement of the tray 4 is such that the tray 4 returns to the same position it was in when the first image was taken. However, while the tray 4 is in the same position, the circular movement has caused the contact lens 1 to be moved from its first position with respect to the container 2 to a second position with respect to the container 2. The movement of the hydrated contact lens 1 with respect to the container 2 may be rotational movement, or translational movement, or rotational and translational movement. The camera 6 then records a second image of the lens 1 and the container 2, which image is sent to the processing unit 7. The process for recording and transmitting the second image is the same or substantially the same as the process for recording and transmitting the first image, as described herein. As the tray, and hence the container, is in the same position as when the first image was taken, the same LED light source 5 and CCD camera 6 are used for the first lens image and the second lens image, reducing any variation in the images that may result from different equipment being used. The LED light source 5 and CCD camera 6 also need not change position and remain stationary during performance of the method.

The following description includes the case where the movement of the contact lens 1 from the first position to the second is rotational only. However, the invention is equally applicable to the case where the movement of the contact lens 1 is both rotational and translational.

The processing unit 7 analyzes the first image or data representing the first image, such as numerical values, to find the edge of the contact lens or the edge of the digital contact lens image. This is done using software attempting to define a radial dark-to-light transition. The steepest point of the transition is defined as the edge. The transition can be determined by calculating numerical differences between data sets corresponding to adjacent regions of the contact lens, and when the difference exceeds a predetermined threshold, the edge of the lens image can be defined. The numerical values of the data sets can correspond to the brightness of the image, the contrast of the image, or both. As an example, the digital lens images or data can be analyzed by executing one or more computer programs that analyze changes in pixel intensity or contrast of the digitized images of the lenses. A standard ellipse fitting algorithm is used to define the location, size and shape of the lens. The coordinates of the lens center can be derived from these. The parameters of the ellipse are the X center, the Y center, the major axis, the minor axis, and the axis angle, for example. As described above, the edge profile is calculated based on the edge gradients of the lens image.

For example, a computer of the image analysis component 12 may include a lens inspection library. The library may be passed the data corresponding to a digital image of the lens being inspected. The library can examine the data and compare the data to predetermined values to determine whether the imaged lens has a defect or is otherwise faulty, and it can return a pass/fail decision for the inspected lens along with more detailed information regarding the reasons for the pass or fail decision. The library includes configuration files which define configuration parameters. For example, the parameters may include without limitation, thresholds which are used to determine whether a lens passes or fails inspection. The inspection library configuration files may contain the rules that are applied to the inspection algorithm. The rules can thus be passed as parameters to the software for execution of the program. Accordingly, an operator of the inspection system can alter the rules without modifying or recompiling the software calling these parameters.

The particular algorithms and software programs used in accordance with the present invention may be practiced using any conventional programming language and rules, as understood in the art. In an embodiment of the invention actually reduced to practice, the inspection algorithms are programmed in C or C++. Although the specific parameters and algorithms used may vary without departing from the spirit of the invention, some parameters may include, and are not limited to, the area of the image to enclose the lens, criteria for calculating rotational movement of the lenses, criteria for rejecting missing lenses, criteria for rejecting bad lens images, criteria for rejecting misshapen or misaligned images, and criteria for rejecting lens edge defects.

The algorithms make use of pixel intensity and contrast levels between defects and the neighboring background area. Different detection and tracking thresholds can be defined depending on the sensitivity needed for lens inspection. Different thresholds are used to detect different types of defects. However, the same threshold value is applied over the entire lens for the detection of a specific defect, irrespective of the curvatures of the lens. In order to use the same threshold, a uniform background is required and is achieved by careful selection of the illumination source and optics, software filtering, or a combination of both. The particular threshold values used for the inspection algorithms can be determined empirically, and optimized to achieve desired lens passage and failure rates.

Using the edge inspection algorithms, it is possible to map the lens edge based on differences in contrast between the lens edge and the background. By providing an algorithm with user defined parameters, such as contrast thresholds, the inspection system provides accurate inspection of lenses with reduced differences in contrast. In other words, the inspection system, which uses 12 bit images, is more sensitive than conventional systems requiring high contrast images, which uses 8 bit images. The edge mapping algorithm also provides for accurate mapping of the lens edge. In addition, it is possible to discriminate between the inner edge and outer edge of the lens edge region, and therefore, it is possible to map both the inner and outer edges of the lens.

The processing unit further measures or determines the radial distance around the circumference of the edge and creates an outer edge plot of the contact lens, which, due to the slight irregularities in the shape of a lens, can result in an outer edge plot or profile as shown in FIG. 3A. An inner edge plot can be generated in a similar manner. The edge profile is filtered to generate a true edge profile, or image of the true lens edge profile. Filtering removes elements that may distort the true edge profile. Examples of elements or effects that may be filtered include short wave effects, such as measurement noise resulting from debris close to the lens edge, and long wave effects, such as distortion of the image resulting from the meniscus of the liquid in which the lens is located, the imaging optics, or both. It can be understood that the edge profile of the lens can be represented numerically or graphically. In FIG. 3A, the edge profile is graphically represented as an edge plot. The processor 7 also performs a thresholding operation to select possible blemishes or other features on the contact lens 1, wherein the location of any features in the image that are darker than a pre-specified darkness are recorded such as based on predetermine threshold values for pixel intensity. Both the outer edge plot of the contact lens and the position and characteristics of possible blemishes or features are stored in the memory 8 of the processor 7.

The processing unit 7 then performs the same analysis on the second image as described for the first image. The edge plot of the lens 1 is recorded as shown in FIG. 3B, together with the position of any possible blemishes as identified by the thresholding operation. If there are no possible blemishes indicated on the first and second images, then the lens 1 is passed. If there are possible blemishes identified on the first and second images then a further analysis is made before the lens 1 is passed or failed. In practice, due to the nature of the container 2 and the liquid 3, it is unusual for there to be no possible blemishes found and nearly all of the lenses inspected will undergo the further analysis. The further analysis is described below.

On occasion the contact lens 1 may be in contact with a portion of the cavity of the container 2. For example, a portion of the contact lens edge may contact a portion of the sidewall of the container cavity. This may result in an edge plot that includes a gap where the light-to-dark transition is not detected. If this is the case, in either the first or second images, the processor 7 ignores this part of the edge plot when making a comparison between the first and second edge plots.

Alternatively, the contact lens can be reinspected if the lens is in contact with the container cavity sidewall during the first inspection process. For example, in a manufacturing line, the container can be redirected through the inspection station and the lens can be reinspected, as described herein. When a lens is reinspected for being in contact with the container cavity sidewall, inspection methods may include a step of centering the lens in the container such that the lens is not in contact with the sidewall during the reinspection. For example, the container may be agitated again to attempt to separate the contact lens from the sidewall, and then the inspection method can be performed as described herein. If the lens ultimately remains stuck to the sidewall, the lens can be rejected.

FIGS. 3A and 3B show an outer edge plot of a typical contact lens in a first and second position respectively. As described herein, an inner edge plot may be represented similarly to that shown in FIGS. 3A and 3B. As described above, even though a contact lens may be free of gross defects, it is sufficiently rotationally asymmetric that a plot made of the outer edge of the lens allows one to see how much a lens has been rotated once it has been moved. FIG. 3A can be understood to be an edge plot of a contact lens in a first position, and FIG. 3B can be understood to be an edge plot of the contact lens of FIG. 3A in a different (rotated) second position. FIGS. 3A and 3B are graphical representations of the plot that will be made by the processor 7 when analyzing the edge of a contact lens, or the edge data of the digital contact lens image, in a first and second position. The X axis is an angular measurement and the Y axis a radial measurement. The X axis refers to the degrees around the contact lens and corresponding to the 0 degree meridian to the 360 degree meridian, as shown in the illustrative lens shown in FIG. 7 where meridians are illustrated in 45 degree increments. As illustrated in FIG. 8, which is an example of a contact lens edge between the 0 degree meridian and the 90 degree meridian, the edge profile is irregular and the linear radial distance varies (i.e., it is not exactly the same) from the 0 degree meridian to the 90 degree meridian. For example, at point 62 of the lens edge in FIG. 8, the linear radial distance (shown by the arrow 9a) has the greatest value, which is similar to the peak observed just before the 90 degree meridian as shown in FIG. 3A (having a radial distance of about 323.6 pixels. Similarly at point 64 of the lens edge in FIG. 8, the linear radial distance (shown by arrow 9b) has the smallest value, which is similar to the valley observed just after the 0 degree meridian as shown in FIG. 3A (having a radial distance of about 320.9 pixels.

When, as described above, the processor 7 has identified possible blemishes on the lens 1, it begins the further analysis of the lens 1. The first step is to cross-correlate the outer edge plots in order to calculate the rotation of the lens 1. In effect, the translation along the angular axis of the profile shown in FIGS. 3A and 3B is measured, thereby obtaining the angular rotation of the lens concerned. The next step of the analysis is described with regard to FIGS. 4A and 4B.

FIGS. 4A and 4B show an example of the images taken by the camera 6 in the situation when the lens 1 includes a blemish. FIG. 4A shows the first image captured by the CCD camera 6 of the lens 1 in the first position relative to the container 2. FIG. 4B shows the second image captured by the CCD camera 6 of the lens 1 in the second position relative to the container 2. As described above, the processor 7 performs a thresholding operation to distinguish features of interest on the edge 32 of the lens 1 and its main surface. The edge of the lens is shown by the approximately circular line 32 with the surface of the lens 31 inside this line. Among the features distinguished by the processor 7 as being over the threshold darkness are the marks or features 33 and 34. The processor 7 stores the characteristics of the marks 33 and 34 such that it can identify the marks in both the first and second images, such as by changes in pixel intensity values, for example. As mentioned above, because the processor has ascertained that there are marks present over the threshold darkness, thereby indicating that there are possible blemishes, the further analysis of the images occurs.

The processor 7 calculates the rotation of the lens 1 as described above. The processor 7 also calculates the polar coordinates of the marks 33 and 34 in the first image and the second image respectively. In an alternative embodiment, the position of the marks may be calculated in Cartesian coordinates. The processor 7 also can determine whether the radial position of the potential defects or marks 33 and 34 is the same before and after rotation. The precision criteria can be predetermined, and suitable values for categorizing the potential defects as being the same include movement less than about 5.0 pixels in either direction from the first position, such as ±4.0 pixels, ±3.0 pixels, ±2.0 pixels, ±1.0 pixel, and the like. In certain embodiments, the threshold is ±2.0 pixels. It can also be understood that the resolution can be a fraction of these values, that is a fraction of a pixel. A comparison of the rotation of the lens 1 and the marks 33 and 34 is then made. If the rotational movement of the lens 1 is the same as that of the marks 33 and 34, those marks are very likely to be present on the contact lens 1 itself. If the rotational movement of the marks is different to that of the contact lens 1, then those marks are not on the lens itself and are present either on the container 2 or in the liquid 3. In this embodiment, the difference in angular shift, in order for a mark to be taken not to be part of the lens, is 1°. This is a variable parameter and may be as little as 0.5° or lower or as much as 5° or higher.

In the case where the minimum angular shift is 1° as described above, the minimum rotation of the contact lens 1 between the first position and second position is 5°. This ensures that it is possible to distinguish between blemishes that have moved with the contact lens 1 and those that have not. Therefore, if the edge plot indicates that the contact lens has not moved more than 5° the contact lens 1 is subjected to the movement of the tray 4 again and at least two images are taken again for comparison, as described above.

In this case, the outer edge plot of the lens 1 indicates that the lens has rotated an angle of θ (which in this case is 56°). The mark 33 has rotated by an angle of α, being 14°. This amount of rotation is deemed to be insignificant, and is significantly less than an angle of θ±1° (i.e. 56°±1°). This indicates that the mark 33 is either in the liquid 3 or the container 2 and is not a blemish present on the contact lens 1. However, mark 34 has rotated an angle of 56°, that is within the range of θ−1° to θ+1°, and is therefore taken as having moved with the lens 1. This indicates that the mark 34 is a blemish present on the contact lens 1 and the contact lens 1 should be rejected.

FIGS. 5A and 5B show a similar set of images as that described for FIGS. 4A and 4B, however in this situation the lens 1' does not include any blemishes. The lens 1' includes a lens surface 41, a lens edge 42 and a mark 43. Also as described above, because there is a possible blemish indicated by the mark 43, the processor uses the outer edge plot of the lens edge 42 to work out the rotational movement of the lens 1' as φ (which in this case is 45°). The processor also calculates the rotational movement of the mark 43, which in this case is β, being 15°, significantly less than φ and certainly not within φ±1° (i.e. 45°±1°). Therefore, this indicates that the mark is not on the contact lens 1' and the lens 1' should be accepted.

It can be understood that the processes described above and illustrated in reference to FIGS. 4A and 4B, and FIGS. 5A and 5B are performed on the numerical data extracted from each lens image (e.g., the data that corresponds to the digital representation of the lens). The processing can be done by conventional techniques, as understood by persons of ordinary skill in the art. For example, the lens edge shape can be determined based on conventional edge detection techniques, such as techniques using a Sobel filter or differentiation, as understood by persons of ordinary skill in the art. These detection techniques are written into software for computers. Examples of suitable machine vision image processing software useful in the present methods include Halcon software from MVTec Software GmbH (Germany), Sapera software from DALSA (Canada), or Common Vision Blox software from STEMMER IMAGING GmbH (Germany).

FIG. 6 shows a lens inspection system according to another embodiment capable of inspecting a large number of lenses simultaneously. The system is arranged in the same way as described for the first embodiment of the invention but with a plurality of lenses, cameras and light sources arranged to operate together. A plurality of contact lenses 61 are in containers containing liquid, in this particular system there are 32 lenses. The contact lenses are arranged on a tray 62 in an 8×4 layout. There is a plurality of light sources (not shown) located under the contact lenses 61. The system further includes a plurality of CCD cameras 63 located above the contact lenses 61 such that they may take an image of the said lenses. In this particular case, there are 16 cameras (only four shown) 63 associated with 16 of the contact lenses 61. The system first performs the analysis of the 16 lenses as described above for a single lens. Then the system is arranged such that an analysis of the remaining 16 lenses is taken after the movement of the tray 62 such that those lenses become associated with the plurality of cameras 63. The system is arranged such that the processing apparatus 64 and memory 65 can store information regarding which of the plurality of lenses have been rejected and which have passed. The lenses that have been passed and the lenses that have been rejected are separated at the end of the inspection process.

In a similar manner to the first embodiment relating to the inspection of one lens, in order to increase the accuracy of the system, the same camera and illumination source is used to take each of the two images taken of one lens. This eliminates any differences that would result in the tolerances of the camera and illumination sources varying between sets. However, it is not essential that the same camera and light source are used to take the first and second images. It may be more efficient to have first camera associated with the lens in a first position and a second camera associated with the lens in a second position, and the movement of the lens between the first and second position being sufficient to create the relative movement with respect to the container holding the lens such that two images may be compared.

As an example, an automated lens inspection system in accordance with the present disclosure can be described as follows.

The system includes a plurality (e.g., 8) of LED light sources which can be either custom made or obtained publicly from companies. One LED light source is provided per lens or per lens container so that there is a one-to-one correlation. A plurality of collimation lenses, such as achromatic doublet lenses, are provided above the LED light sources, with one collimation lens being located above one LED light source. An example of collimation lenses useful in the present system includes 45-140 lens from Edmund Optics (United Kingdom). A plurality of digital CCD cameras, such as the Scout scA1400-17gm camera from Basler (Germany), are positioned to receive light passing through the collimation lenses from the LED light sources. Each camera is connected by a gigabit Ethernet connection to a single computer or a plurality of computers. Typically 8 cameras are connected to a network switch which connects to 4 PC servers wherein each server receives data from 2 cameras. The computers can be computer servers or workstations. These computers or additional computers attached to these computers may be provided with other conventional data input and data output devices, such as keyboards, mice, data displays, such as monitors, network switches, modems, and power supplies. The elements of the system can be coupled together using conventional techniques.

Each camera is responsible for analyzing one lens position in the tray (see FIG. 6). Each camera includes one or more data communication ports, such as Ethernet ports, which are configured to receive image data from, and to control settings of, the camera. One example of an Ethernet card useful in the present systems includes the gigabit Ethernet port, which is standard on several commercially available servers, such as Dell servers. Each of the computers may also include a digital input/output (I/O) card that is connected to a programmable logic controller to help control movement of the lenses relative to the cameras and to control the image capture of the lenses.

A lighting controller provides programmable control of the LED light sources. The control may be provided via any suitable interface, such as an USB interface. The lighting controller causes the LED light source (e.g., controls the intensity of the LED light source) to illuminate based on a defined current of the controller's LED outputs. The cameras obtain images continuously at a pre-determined rate, such as about 17 frames/second. When a lens is in position for inspection, a trigger is activated by the program logic controller in the computer to grab and store the lens image data in the computer memory. The images have a resolution of 1024× 1024 pixels and 4096 grey levels.

The tray is placed on a carrier that can move the tray to cause rotation of the contact lens in the contact lens containers. The carrier can move through a circular arc of about 20 mm to about 30 mm radius (e.g., about 25 mm radius). The movement can be performed manually or through automated means. A locking device, such as a spring loaded locking pin can lock the tray in position under the camera after the tray motion is completed.

A method using this system can comprise, consist essentially of, or consist entirely of the following steps in this order: (i) move the tray with the contact lens-containing containers thereon to induce rotation of the contact lenses in the containers; (ii) capture first and second images of one hydrated contact lens at an interval of about one second between the first and second images; (iii) inspect both images for potential lens defects using lens inspection software; (iv) calculate the edge profiles using the software described herein; (v) perform a cross-correlation between the edge profile of the first image and the edge profile of the second image to find the relative angle of movement; (vi) convert the position of all features to polar coordinates; (vii) offset the polar coordinates by the relative angle found in step (v); and (vii) search for matched pairs of defects. If a lens defect is detected, the lens is rejected. If the potential defect is determined to be an artifact, the lens is passed and further processed.

After the images are acquired, the tray with lens containers, is moved to a downstream processing station where the container can be sealed, such as hermetically or heat sealed with a foil containing sealing member for contact lens blister packs, if the container contains an acceptable lens. After sealing, the containers with acceptable lenses can be sterilized (e.g., terminally sterilized), such as by autoclaving a or exposure to gamma radiation at a subsequent lens manufacturing station. In some situations, UV radiation may be used to sterilize the lenses in the containers, but the UV radiation is typically provided before the container is sealed.

As described herein, if the lens is in contact with a cavity sidewall, the lens can be reinspected using the methods described herein, after one or more attempts to dislodge the lens from the sidewall are performed. If no defects are detected in the reinspected lenses, they can pass to the packaging and sterilization steps described above.

In addition, the present methods can include steps of acquiring at least one more image of the lens, such as a total of three or more images of the lenses being inspected, to help reduce ambiguity in the data and facilitate accurate inspection.

While the present invention has been described and illustrated with reference to particular embodiments, it will be appreciated by those of ordinary skill in the art that the invention lends itself to many different variations not specifically illustrated herein. Certain variations are described above and further variations are described by way of example below.

As mentioned above, the examples described detail on the case where the movement of the lens from the first position to the second position is rotational. However, the lens may experience both rotational and translational movement between the first position and second position. Just as the rotation of a possible blemish between the first position and second position is compared to the rotation of the lens between the first position and second position, the processing unit may also compare the translation of a possible blemish to the translation of the lens.

During the thresholding operation whereby possible blemishes are identified on a lens, further selection criteria may be specified; such as selection due to size, orientation and/or shape of the possible blemishes.

In the process as described above the rotation of the contact lens is determined by analyzing the edge plot of the contact lens independent of any normal feature on the contact lens, such as an identification mark and the like. In an alternative embodiment, there may be a mark deliberately provided on a surface of the lens that acts as a reference point. Rather than create an edge plot, or in addition to creating the edge plot, the processing of the image could determine the rotation of the lens between the first and second position by determining how much the identification mark has rotated. In a yet further embodiment, if the contact lens is a toric contact lens there is usually a line or other identification mark that indicates the orientation of the axis of the cylinder as well as ballasting to ensure the correct orientation of the lens in the eye. These features could be used as reference marks by which the rotation of the lens may be determined. Examples of identification marks provided on ophthalmic lenses, such as contact lenses, are illustrated in FIGS. 9A, 9B, 9C, and 9D. FIG. 9A illustrates a single identification mark provided on the 270 degree meridian (see FIG. 7 for example). FIG. 9B illustrates three identification marks, with a central mark being provided on the 270 degree meridian and located between two other identification marks, each being spaced apart by about 10-30 degrees from the 270 degree meridian. FIG. 9C illustrates an identification mark that comprises text. The text can be formed from one or more holes or indentations in a lens surface. FIG. 9D illustrates four identification marks, where the three inferior most marks are similar to FIG. 9B, and one additional identification mark is horizontally oriented along the 180 degree meridian.

Although the disclosure herein refers to certain specific embodiments, it is to be understood that these embodiments are presented by way of example and not by way of limitation. Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment disclosed herein. The intent of the foregoing detailed description, although discussing exemplary embodiments, is to be construed to cover all modifications, alternatives, and equivalents of the embodiments described in the present description and claims.

What is claimed is:

1. A method of inspecting an ophthalmic lens for defects, comprising;
    providing an ophthalmic lens in a volume of liquid in a cavity of a container;
    obtaining a first image of the ophthalmic lens at a first position in the container, the first image comprising a first image of a center of the ophthalmic lens and a first image of a lens edge of the entire ophthalmic lens, the lens edge including an outer peripheral edge of the ophthalmic lens, or an inner edge of the ophthalmic lens, or a distance between the outer peripheral edge and the inner edge of the ophthalmic lens, or combinations thereof;
    causing the ophthalmic lens to move from the first position in the container to a second position in the container;
    obtaining a second image of the ophthalmic lens at the second position, the second image comprising a second image of the center of the ophthalmic lens and a second image of the lens edge of the entire ophthalmic lens, the lens edge including the outer peripheral edge of the ophthalmic lens, or the inner edge of the ophthalmic lens, or the distance between the outer peripheral edge and the inner edge of the ophthalmic lens, or combinations thereof;

processing the first image and second image with a computer algorithm to locate features in the images;

generating a first lens edge profile from the first image by measuring first image linear radial distances around a perimeter of the first image of the lens, each first image linear radial distance being measured from the first image of the center of the ophthalmic lens to the first image of the lens edge, wherein the lens edge used for the measuring is one of the outer peripheral edge of the ophthalmic lens, or the inner edge of the ophthalmic lens, or both, all of the first image linear radial distances are measured using the same lens edge, and the first image linear radial distances so measured vary around the perimeter of the lens;

generating a second lens edge profile from the second image by measuring second image lens linear radial distances around a perimeter of the second image of the lens, each second image linear radial distance being measured from the second image of the center of the ophthalmic lens to the second image of the lens edge, wherein the lens edge used for the measuring is one of the outer peripheral edge of the ophthalmic lens, or the inner edge of the ophthalmic lens, or both, all of the second image linear radial distances are measured using the same lens edge, the second image linear radial distances are measured using the same lens edge as the first image linear radial distances, and the second image linear radial distances so measured vary around the perimeter of the lens;

determining an amount of rotational, movement of the lens from the first position to the second position by calculating a first and second image lens angular shift between the first lens edge profile and the second lens edge profile;

calculating a first and second image feature angular shift between a corresponding feature located in the first and second images;

distinguishing a feature that has moved with the lens from a feature that has not moved with the lens by comparing the first and second image lens angular shift to the first and second image feature angular shift of the corresponding feature;

classifying the corresponding feature that has the first and second image feature angular shift within about ±5 degrees of the lens angular shift, and is not a normal lens feature, as a lens defect; and rejecting the lens if the lens includes a pre-determined number of lens defects.

2. The method of claim 1, wherein the step of processing the first image and the second image with a computer algorithm to locate features in the images locates features comprising potential lens defects in both the first image and the second image, and the step of calculating the first and second image feature angular shift between the corresponding feature located in the first and second images is conducted only when the potential lens defects are detected in both the first image and the second images.

3. The method of claim 1, wherein the step of causing the lens to move from the first position to the second position comprises causing movement of the lens relative to the container.

4. The method of claim 1, wherein the step of causing the lens to move from the first position to the second position comprises rotational lens movement or translational lens movement, or both.

5. The method of claim 1, wherein the step of causing the lens to move from the first position to the second position comprises rotating the container, vibrating the container, or both.

6. The method of claim 1, wherein the step of processing the first image and second image with a computer algorithm to locate features in the images comprises thresholding the first and second images to locate the features in the images.

7. The method of claim 1, wherein the step of processing the first image and second image with a computer algorithm to locate features in the images comprises identifying the outer peripheral edge, or the inner edge, or the distance between the outer peripheral edge and the inner edge, or combinations thereof in the first and second images and locating a deviation from an expected lens edge shape, the deviation being identified as a potential lens defect.

8. The method of claim 1, wherein the container is in a first location when the first image is obtained and in a second, different location when the second image is obtained.

9. The method of claim 1, wherein the ophthalmic lens comprises an identification mark and the identification mark is one of the features located in the first and second images.

10. The method of claim 9, wherein the lens comprises at least one additional feature other than the identification mark.

11. The method of claim 1, wherein the first and second images are obtained using at least one camera.

12. The method of claim 11, wherein the at least one camera includes a complementary metal oxide semiconductor (CMOS) integrated circuit, a charge-coupled device (CCD) array, or both for recording the images.

13. The method of claim 11, wherein the camera is arranged to have a depth of field sufficiently large to acquire an image in which both the lens edge and the lens surface are in focus simultaneously.

14. The method of claim 1, wherein the steps of obtaining the first image of the ophthalmic lens at the first position and obtaining the second image of the ophthalmic lens at the second position comprise generating a bright field image of the ophthalmic lens with a light source.

15. The method of claim 14, wherein the steps of obtaining the first image of the ophthalmic lens at the first position and obtaining the second image of the ophthalmic lens at the second position further comprise producing collimated light from the light source with a collimating lens and directing the collimated light to a camera.

16. The method of claim 15, wherein the step of producing collimated light from the light source includes partially collimating the light from the light source with said collimating lens, and then using the container and the liquid in container to complete collimation of the partially collimated light from the light source.

17. The method of claim 1, wherein the step of distinguishing the feature that has moved with the lens from the feature that has not moved with the lens further comprises classifying a feature that moves by more than a minimum angular shift relative to the ophthalmic lens as a non-lens feature.

18. The method of claim 1, herein the first and second lens edge profiles are generated using computer software.

19. The method of claim 1, further comprising providing, a plurality of containers, each container comprising a single ophthalmic lens, and inspecting the plurality of lenses for defects simultaneously.

20. The method of claim 19, wherein the plurality of containers are provided in a linear arrangement.

21. An automated ophthalmic lens inspection system comprising: a camera; a light source; a carrier capable of moving an ophthalmic lens in a lens container from a first position in the container to a second position, the camera being arranged to receive light from the light source via the lens carrier; and a processing unit for receiving first and second lens images taken by the camera, the processing unit having a first processing module for detecting features in the images taken by the camera; a second processing module for ascertaining movement of the lens by comparing a first lens edge profile generated from the first lens image and a second lens edge profile generated from the second lens image, the first lens edge profile is generated by the processing unit from the first lens image by measuring first image linear radial distances around a perimeter of the lens in the first image, each first image linear radial distance being a measurement from a center of the lens in the first image to a lens edge in the first image, wherein the lens edge used for the measurement is one of an outer peripheral edge of the lens, or an inner edge of the lens, or both, all of the first image linear radial distances are measured using the same lens edge, and the first image linear radial distances so measured vary around the perimeter of the lens, and the second lens edge profile is generated by processing unit from the second lens image by measuring second image linear radial distances around the perimeter of the lens in the second image, each second image linear radial distance being a measurement from the center of the lens in the second image to the lens edge in the second image, wherein the lens edge used for the measurement is one of the outer peripheral edge of the lens, or the inner edge of the lens, or both, all of the second image linear radial distances are measured using the same lens edge, the second image linear radial distances are measured using the same lens edge as the first image linear radial distances, and the second linear radial distances so measured vary around the perimeter of the lens; and a third processing module for comparing the movement of the features detected by the first processing module to the movement of the lens as ascertained by the second processing module by calculating, at least in part, a first and second image lens angular shift between, the first lens edge profile and the second lens edge profile.

22. The method of claim 1, wherein the first and second images are obtained using one camera.

23. The method of claim 1, further comprising the steps of:
determining, based on the determined amount of rotational movement of the lens from the first position to the second position, if the ophthalmic lens moved more than ±5°, and, if the ophthalmic lens did not move more than ±5°, causing the ophthalmic lens to move from the second position in the container to a third position in the container and obtaining a third image of the ophthalmic lens at the third position, the third image comprising a third image of the center of the ophthalmic lens and a third image of the lens edge of the entire ophthalmic lens, the lens edge including the outer peripheral edge of the ophthalmic lens, or the inner edge of the ophthalmic lens, or the distance between the outer peripheral edge and the inner edge of the ophthalmic lens, or combinations thereof;

generating a third lens edge profile from the third image by measuring third image linear radial distances around a perimeter of the third image of the lens, each third image linear radial, distance being measured from the third image of the center of the ophthalmic lens to the third image of the lens edge, wherein the lens edge used for the measuring is one of the outer peripheral edge of the ophthalmic lens, or the inner edge of the ophthalmic lens, or both, all of the third image linear radial distances are measured using the same lens edge, the third image linear radial distances are measured using the same lens edge as the first image linear radial distances, and the third image linear radial distances so measured vary around the perimeter of the lens; and determining an amount of rotational movement of the lens from the first position to the third position by calculating a first and third image lens angular shift between the first lens edge profile and the third lens edge profile;

calculating a first and third image feature angular shift between a corresponding features located in the first and third images;

distinguishing a feature that has moved with the lens from a feature that has not moved with the lens by comparing the first and third image lens angular shift to the first and third feature angular shift of the corresponding feature;

classifying the corresponding feature that has the first and third image feature angular shift within about ±5 degrees of the lens angular shift, and is not a normal lens feature, as a lens defect; and rejecting the lens if the lens includes a pre-determined number of lens defects.

24. The method of claim 1, further comprising obtaining a third image and a fourth image of the ophthalmic lens.

25. The method of claim 1, wherein a lens defect is classified as a feature that has an angular shift within about ±1 degree of the lens angular shift, and is not a normal lens feature.

* * * * *

UNITED STATES PATENT AND TRADEMARK OFFICE
CERTIFICATE OF CORRECTION

| | | |
|---|---|---|
| PATENT NO. | : 7,990,531 B2 | Page 1 of 2 |
| APPLICATION NO. | : 12/133596 | |
| DATED | : August 2, 2011 | |
| INVENTOR(S) | : Julie Ann Clements et al. | |

It is certified that error appears in the above-identified patent and that said Letters Patent is hereby corrected as shown below:

In column 1, line 37, delete "tenses" and insert -- lenses --, therefor.

In column 3, line 37, delete "thus" and insert -- thus, --, therefor.

In column 4, line 46, delete "When" and insert -- when --, therefor.

In column 6, line 33, delete "position" and insert -- position, --, therefor.

In column 7, line 38, delete "Lens" and insert -- lens --, therefor.

In column 9, line 53, delete "extraction hydration" and insert -- extraction/hydration --, therefor.

In column 12, line 5, delete "narfilcon" and insert -- narafilcon --, therefor.

In column 12, line 6, delete "(BIOFTNITY," and insert -- (BIOFINITY, --, therefor.

In column 12, line 24, delete "A the liquid 3," and insert -- 3, the liquid 3 --, therefor.

In column 12, line 58, delete "embodiments" and insert -- embodiments, --, therefor.

In column 15, line 2, delete "recorded" and insert -- recorded, --, therefor.

In column 16, line 2, delete "pixels." and insert -- pixels). --, therefor

In column 16, line 2, delete "Similarly" and insert -- Similarly, --, therefor.

In column 16, line 6, "pixels." and insert -- pixels). --, therefor.

In column 19, line 30, after "autoclaving" delete "a".

In column 20, line 48, in Claim 1, delete "comprising;" and insert -- comprising: --, therefor.

In column 21, line 14, in Claim 1, delete "both," and insert -- both; wherein --, therefor.

In column 21, line 27, in Claim 1, delete "both," and insert -- both; wherein --, therefor.

In column 21, line 34, in Claim 1, delete "rotational," and insert -- rotational --, therefor.

In column 22, line 26, in Claim 9, delete "mark" and insert -- mark, --, therefor.

In column 22, line 54, in Claim 16, after "liquid in" insert -- the --.

In column 22, line 62, in Claim 18, delete "herein" and insert -- wherein --, therefor.

In column 22, line 64, in Claim 19, delete "providing," and insert -- providing --, therefor.

Signed and Sealed this
Tenth Day of April, 2012

David J. Kappos
*Director of the United States Patent and Trademark Office*

CERTIFICATE OF CORRECTION (continued)
U.S. Pat. No. 7,990,531 B2

In column 23, line 22, in Claim 21, delete "both," and insert -- both; wherein --, therefor.

In column 23, line 25, in Claim 21, after "generated by" insert -- the --.

In column 23, line 32, in Claim 21, delete "both," and insert -- both; wherein --, therefor.

In column 23, line 42, in Claim 21, delete "between," and insert -- between --, therefor.

In column 24, line 15, in Claim 23, delete "radial," and insert -- radial --, therefor.

In column 24, line 20, in Claim 23, delete "both," and insert -- both; wherein --, therefor.